(12) United States Patent
Vardi et al.

(10) Patent No.: US 7,850,725 B2
(45) Date of Patent: *Dec. 14, 2010

(54) EXTENDIBLE STENT APPARATUS

(75) Inventors: Gil Vardi, Chesterfield, MO (US);
Charles Davidson, Winnetka, IL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 464 days.

This patent is subject to a terminal disclaimer.

(21) Appl. No.: 11/453,390

(22) Filed: Jun. 15, 2006

(65) Prior Publication Data

US 2006/0241740 A1    Oct. 26, 2006

Related U.S. Application Data

(63) Continuation of application No. 10/440,401, filed on May 19, 2003, now Pat. No. 7,766,955, which is a continuation of application No. 09/750,372, filed on Dec. 27, 2000, now Pat. No. 6,599,316, which is a continuation-in-part of application No. 09/007,265, filed on Jan. 14, 1998, now Pat. No. 6,210,429, which is a continuation-in-part of application No. 08/744,002, filed on Nov. 4, 1996, now abandoned.

(51) Int. Cl.
*A61F 2/06* (2006.01)

(52) U.S. Cl. ..................... 623/1.15; 623/1.16; 623/1.35

(58) Field of Classification Search ....... 623/1.14–1.16, 623/1.34, 1.35, 1.21, 1.23; 606/191, 194, 606/198, 153

See application file for complete search history.

(56) References Cited

U.S. PATENT DOCUMENTS 1,596,754 A    8/1926    Moschelle
3,657,744 A    4/1972    Ersek (Continued)

FOREIGN PATENT DOCUMENTS

CA    2318314    1/1999

(Continued)

OTHER PUBLICATIONS

U.S. Appl. No. 09/663,111, filed Sep. 15, 2000, Davidson et al.

(Continued)

*Primary Examiner*—Paul Prebilic
(74) *Attorney, Agent, or Firm*—Vidas, Arrett & Steinkraus, P.A.

(57) ABSTRACT

The present invention concerns novel stent apparatuses for use in treating lesions at or near the bifurcation point in bifurcated cardiac, coronary, renal, peripheral vascular, gastrointestinal, pulmonary, urinary and neurovascular vessels and brain vessels. More particularly, the invention concerns a stent apparatus with at least one side opening which may further comprise an extendable stent portion laterally extending from the side opening and at least partly in registry with the wall of the side opening. Devices constructed in accordance with the invention include, singularly or in combination, a main expandable stent comprising at least one substantially circular side opening located between its proximal and distal end openings, which side opening may further comprise an expandable portion extending radially outward from the edges of the side opening; and a branch stent comprising proximal and distal end openings and which may further comprise a contacting portion at its proximal end, and which may optionally be constructed to form either a perpendicular branch or a non-perpendicular branch when inserted through a side opening of the main stent. The stents of the invention are marked with, or at least partially constructed of, a material which is imageable during intraluminal catheterization techniques, most preferably but not limited to ultrasound and x-ray.

16 Claims, 6 Drawing Sheets

U.S. PATENT DOCUMENTS

| | | | |
|---|---|---|---|
| 3,872,893 A | 3/1975 | Roberts | |
| 4,140,126 A | 2/1979 | Choudhury | |
| 4,309,994 A | 1/1982 | Grunwald | |
| 4,410,476 A | 10/1983 | Redding et al. | |
| 4,413,989 A | 11/1983 | Schjeldahl et al. | |
| 4,421,810 A | 12/1983 | Rasmussen | |
| 4,453,545 A | 6/1984 | Inoue | |
| 4,503,569 A | 3/1985 | Dotter | |
| 4,552,554 A | 11/1985 | Gould et al. | |
| 4,681,570 A | 7/1987 | Dalton | |
| 4,689,174 A | 8/1987 | Lupke | |
| 4,731,055 A | 3/1988 | Melinyshyn et al. | |
| 4,733,665 A | 3/1988 | Palmaz | |
| 4,739,762 A | 4/1988 | Palmaz | |
| 4,742,128 A | 5/1988 | Frisch et al. | |
| 4,759,748 A | 7/1988 | Reed | |
| 4,762,128 A | 8/1988 | Rosenbluth | |
| 4,769,005 A * | 9/1988 | Ginsburg et al. | 604/510 |
| 4,769,029 A | 9/1988 | Patel | |
| 4,774,949 A * | 10/1988 | Fogarty | 606/108 |
| 4,795,465 A * | 1/1989 | Marten | 623/9 |
| 4,819,664 A | 4/1989 | Nazari | |
| 4,872,874 A | 10/1989 | Taheri | |
| 4,878,495 A | 11/1989 | Grayzel | |
| 4,896,670 A | 1/1990 | Crittenden | |
| 4,900,314 A | 2/1990 | Quackenbush | |
| 4,905,667 A * | 3/1990 | Foerster et al. | 600/104 |
| 4,906,244 A | 3/1990 | Pinchuk et al. | |
| 4,909,258 A | 3/1990 | Kuntz et al. | |
| 4,957,501 A | 9/1990 | Lahille et al. | |
| 4,957,508 A | 9/1990 | Kaneko et al. | |
| 4,964,850 A | 10/1990 | Bouton et al. | |
| 4,983,167 A | 1/1991 | Sahota | |
| 4,994,071 A | 2/1991 | MacGregor | |
| 5,042,976 A | 8/1991 | Ishitsu et al. | |
| 5,054,501 A | 10/1991 | Chuttani et al. | |
| 5,059,177 A | 10/1991 | Towne et al. | |
| 5,061,240 A | 10/1991 | Cherian | |
| 5,064,435 A | 11/1991 | Porter | |
| 5,102,403 A | 4/1992 | Alt | |
| 5,102,417 A | 4/1992 | Palmaz | |
| 5,104,404 A | 4/1992 | Wolff | |
| 5,117,831 A | 6/1992 | Jang et al. | |
| 5,122,125 A | 6/1992 | Deuss | |
| 5,135,536 A | 8/1992 | Hillstead | |
| 5,147,317 A | 9/1992 | Shank et al. | |
| 5,159,920 A | 11/1992 | Condon et al. | |
| 5,176,617 A | 1/1993 | Fischell et al. | |
| 5,192,297 A | 3/1993 | Hull | |
| 5,217,440 A | 6/1993 | Frassica | |
| 5,244,619 A | 9/1993 | Burnham | |
| 5,257,974 A | 11/1993 | Cox | |
| 5,263,932 A | 11/1993 | Jang | |
| 5,282,472 A | 2/1994 | Companion et al. | |
| 5,304,220 A | 4/1994 | Maginot | |
| 5,320,605 A | 6/1994 | Sahota | |
| 5,324,257 A | 6/1994 | Osborne et al. | |
| 5,337,733 A | 8/1994 | Bauerfeind et al. | |
| 5,338,300 A | 8/1994 | Cox | |
| 5,342,295 A | 8/1994 | Imran | |
| 5,342,297 A | 8/1994 | Jang | |
| 5,342,387 A * | 8/1994 | Summers | 606/198 |
| 5,350,395 A | 9/1994 | Yock | |
| 5,383,892 A | 1/1995 | Cardon et al. | |
| 5,387,235 A | 2/1995 | Chuter | |
| 5,395,332 A | 3/1995 | Reesemann et al. | |
| 5,395,334 A | 3/1995 | Keith et al. | |
| 5,397,355 A * | 3/1995 | Marin et al. | 623/1.2 |
| 5,404,887 A | 4/1995 | Prather | |
| 5,409,458 A | 4/1995 | Khairkhahan et al. | |
| 5,413,581 A | 5/1995 | Goy | |
| 5,413,586 A | 5/1995 | Dibie et al. | |
| 5,417,208 A | 5/1995 | Winkler | |
| 5,437,638 A | 8/1995 | Bowman | |
| 5,441,515 A * | 8/1995 | Khosravi et al. | 606/194 |
| 5,443,497 A | 8/1995 | Venbrux | |
| 5,445,624 A | 8/1995 | Jimenez | |
| 5,449,373 A | 9/1995 | Pinchasik et al. | |
| 5,449,382 A | 9/1995 | Dayton | |
| 5,456,694 A | 10/1995 | Marin et al. | |
| 5,456,712 A | 10/1995 | Maginot | |
| 5,456,714 A | 10/1995 | Owen | |
| 5,458,605 A | 10/1995 | Dlemm | |
| 5,462,530 A | 10/1995 | Jang | |
| 5,476,471 A * | 12/1995 | Shifrin et al. | 606/151 |
| 5,487,730 A | 1/1996 | Marcadis et al. | 604/96 |
| 5,489,271 A | 2/1996 | Andersen | |
| 5,489,295 A | 2/1996 | Piplani et al. | |
| 5,496,292 A | 3/1996 | Burnham | |
| 5,505,702 A | 4/1996 | Arney | |
| 5,507,768 A | 4/1996 | Lau et al. | |
| 5,507,769 A | 4/1996 | Marin et al. | |
| 5,514,154 A * | 5/1996 | Lau et al. | 623/1.15 |
| 5,522,801 A | 6/1996 | Wang | |
| 5,531,788 A | 7/1996 | Dibie et al. | |
| 5,545,132 A | 8/1996 | Fagan et al. | |
| 5,549,553 A | 8/1996 | Ressemann et al. | |
| 5,549,554 A | 8/1996 | Miraki | |
| 5,562,620 A | 10/1996 | Klein et al. | |
| 5,562,724 A | 10/1996 | Vorwerk et al. | |
| 5,562,725 A | 10/1996 | Schmitt et al. | |
| 5,569,295 A | 10/1996 | Lam | |
| 5,571,087 A | 11/1996 | Ressemann et al. | |
| 5,575,771 A | 11/1996 | Walinsky | |
| 5,575,818 A | 11/1996 | Pinchuk | |
| 5,591,197 A * | 1/1997 | Orth et al. | 623/1.16 |
| 5,591,228 A | 1/1997 | Edoga | |
| 5,593,442 A | 1/1997 | Klein | |
| 5,607,444 A | 3/1997 | Lam | |
| 5,609,605 A * | 3/1997 | Marshall et al. | 623/1.11 |
| 5,609,625 A | 3/1997 | Piplani et al. | |
| 5,609,627 A | 3/1997 | Goicoechea et al. | |
| 5,609,629 A | 3/1997 | Fearnot et al. | |
| 5,613,949 A | 3/1997 | Miraki | |
| 5,613,980 A | 3/1997 | Chauhan | |
| 5,613,981 A | 3/1997 | Boyle et al. | |
| 5,617,878 A * | 4/1997 | Taheri | 128/898 |
| 5,626,600 A | 5/1997 | Horzewski et al. | |
| 5,628,788 A | 5/1997 | Pinchuk | |
| 5,632,762 A | 5/1997 | Myler | |
| 5,632,763 A | 5/1997 | Glastra | |
| 5,632,772 A | 5/1997 | Alcime et al. | |
| 5,634,902 A | 6/1997 | Johnson | |
| 5,636,641 A | 6/1997 | Fariabi | 600/585 |
| 5,639,278 A | 6/1997 | Dereume et al. | |
| 5,643,340 A | 7/1997 | Nunokawa | |
| 5,653,743 A | 8/1997 | Martin | |
| 5,662,614 A | 9/1997 | Edoga | |
| 5,669,924 A | 9/1997 | Shaknovich | |
| 5,669,932 A | 9/1997 | Fischell et al. | |
| 5,676,696 A | 10/1997 | Marcade | |
| 5,676,697 A * | 10/1997 | McDonald | 623/1.35 |
| 5,679,400 A | 10/1997 | Tuch | |
| 5,683,450 A * | 11/1997 | Goicoechea et al. | 606/194 |
| 5,690,642 A | 11/1997 | Osborne et al. | |
| 5,693,084 A | 12/1997 | Chuter | |
| 5,693,086 A | 12/1997 | Goicoechea et al. | |
| 5,697,971 A * | 12/1997 | Fischell et al. | 623/1.15 |
| 5,707,348 A | 1/1998 | Krogh | 602/41 |
| 5,707,354 A | 1/1998 | Salmon et al. | |
| 5,709,713 A | 1/1998 | Evans et al. | |
| 5,716,365 A | 2/1998 | Goicoechea et al. | |
| 5,718,683 A | 2/1998 | Ressemann et al. | |
| 5,718,724 A | 2/1998 | Goicoechea et al. | |

| | | | | | | |
|---|---|---|---|---|---|---|
| 5,720,735 | A | 2/1998 | Dorros | 6,039,749 | A | 3/2000 | Marin et al. |
| 5,723,004 | A | 3/1998 | Dereume et al. | 6,042,597 | A | 3/2000 | Kveen et al. |
| 5,724,977 | A | 3/1998 | Yock et al. | 6,045,557 | A | 4/2000 | White et al. |
| 5,728,158 | A | 3/1998 | Lau et al. | 6,048,361 | A | 4/2000 | Von Oepen |
| 5,733,303 | A | 3/1998 | Israel et al. | 6,056,775 | A | 5/2000 | Borghi et al. |
| 5,735,893 | A | 4/1998 | Lau et al. | 6,059,823 | A | 5/2000 | Holman et al. |
| 5,746,766 | A | 5/1998 | Edoga | 6,059,824 | A | 5/2000 | Taheri |
| 5,749,825 | A * | 5/1998 | Fischell et al. .................. 600/3 | 6,066,168 | A | 5/2000 | Lau et al. |
| 5,749,848 | A | 5/1998 | Jang et al. | 6,068,655 | A | 5/2000 | Sequin et al. |
| 5,749,890 | A * | 5/1998 | Shaknovich ................ 606/198 | 6,071,285 | A | 6/2000 | Lashinski et al. |
| 5,755,734 | A | 5/1998 | Richter et al. | 6,086,611 | A | 7/2000 | Duffy et al. |
| 5,755,735 | A | 5/1998 | Richter et al. | 6,090,127 | A | 7/2000 | Globerman |
| 5,755,770 | A | 5/1998 | Ravenscroft | 6,090,128 | A | 7/2000 | Douglas |
| 5,755,771 | A | 5/1998 | Pen et al. | 6,093,203 | A * | 7/2000 | Uflacker .................... 623/1.12 |
| 5,755,773 | A * | 5/1998 | Evans et al. ................. 606/194 | 6,096,073 | A | 8/2000 | Webster et al. |
| 5,755,778 | A * | 5/1998 | Kleshinski ................ 623/1.13 | 6,099,497 | A | 8/2000 | Adams et al. |
| 5,762,631 | A | 6/1998 | Klein | 6,113,579 | A * | 9/2000 | Eidenschink et al. ........ 604/264 |
| 5,776,101 | A | 7/1998 | Goy | 6,117,117 | A | 9/2000 | Mauch |
| 5,776,161 | A | 7/1998 | Globerman | 6,117,156 | A | 9/2000 | Richter et al. |
| 5,776,180 | A | 7/1998 | Goicoechea et al. | 6,129,738 | A | 10/2000 | Lashinski et al. |
| 5,782,906 | A * | 7/1998 | Marshall et al. ............ 623/1.15 | 6,129,754 | A | 10/2000 | Kanesaka et al. |
| 5,800,450 | A | 9/1998 | Lary et al. | 6,142,973 | A | 11/2000 | Carleton et al. |
| 5,800,508 | A | 9/1998 | Goicoechea et al. | 6,143,002 | A * | 11/2000 | Vietmeier .................... 606/108 |
| 5,800,526 | A * | 9/1998 | Anderson et al. .......... 623/1.16 | 6,152,945 | A | 11/2000 | Bachinski et al. |
| 5,814,061 | A | 9/1998 | Osborne et al. | 6,159,238 | A * | 12/2000 | Killion et al. ............... 623/1.11 |
| 5,817,126 | A * | 10/1998 | Imran ......................... 623/1.15 | 6,165,195 | A * | 12/2000 | Wilson et al. ............... 606/194 |
| 5,824,008 | A | 10/1998 | Bolduc et al. | 6,165,197 | A | 12/2000 | Yock |
| 5,824,036 | A | 10/1998 | Lauterjung | 6,168,621 | B1 * | 1/2001 | Vrba .......................... 623/1.2 |
| 5,824,040 | A | 10/1998 | Cox et al. | 6,179,867 | B1 | 1/2001 | Cox |
| 5,824,044 | A | 10/1998 | Quiachon et al. | 6,183,509 | B1 * | 2/2001 | Dibie .......................... 623/1.35 |
| 5,824,045 | A * | 10/1998 | Alt ............................ 623/1.15 | 6,190,403 | B1 | 2/2001 | Rischell et al. |
| 5,827,320 | A | 10/1998 | Richter et al. | 6,203,568 | B1 * | 3/2001 | Lombardi et al. .......... 623/1.13 |
| 5,833,650 | A | 11/1998 | Imran | 6,203,569 | B1 | 3/2001 | Wijay |
| 5,836,966 | A | 11/1998 | St. Germain | 6,210,380 | B1 | 4/2001 | Mauch |
| 5,837,008 | A | 11/1998 | Berg et al. | 6,210,429 | B1 * | 4/2001 | Vardi et al. ................. 623/1.11 |
| 5,843,031 | A | 12/1998 | Hermann et al. | 6,210,433 | B1 * | 4/2001 | Larre ........................ 623/1.15 |
| 5,843,160 | A | 12/1998 | Rhodes | 6,217,527 | B1 | 4/2001 | Selmon et al. |
| 5,843,164 | A | 12/1998 | Frantzen et al. | 6,217,608 | B1 | 4/2001 | Penn et al. |
| 5,846,204 | A | 12/1998 | Solomon | 6,221,080 | B1 | 4/2001 | Power |
| 5,851,210 | A | 12/1998 | Torossian | 6,221,090 | B1 | 4/2001 | Wilson |
| 5,851,464 | A | 12/1998 | Davila et al. | 6,221,098 | B1 | 4/2001 | Wilson et al. |
| 5,855,600 | A | 1/1999 | Alt | 6,231,110 | B1 * | 5/2001 | Umeda et al. .......... 296/146.14 |
| 5,855,601 | A | 1/1999 | Bessler et al. | 6,231,111 | B1 * | 5/2001 | Carter et al. ............ 296/146.15 |
| 5,865,178 | A | 2/1999 | Yock | 6,231,115 | B1 * | 5/2001 | Crean .......................... 296/171 |
| 5,868,777 | A | 2/1999 | Lam | 6,231,563 | B1 | 5/2001 | White et al. |
| 5,871,537 | A | 2/1999 | Holman et al. | 6,231,598 | B1 | 5/2001 | Berry et al. |
| 5,891,133 | A | 4/1999 | Murphy-Chutorian | 6,231,600 | B1 | 5/2001 | Zhong |
| 5,893,887 | A * | 4/1999 | Jayaraman ................ 623/1.15 | 6,235,051 | B1 | 5/2001 | Murphy |
| 5,897,588 | A | 4/1999 | Hull et al. | 6,241,762 | B1 | 6/2001 | Shanley |
| 5,906,640 | A | 5/1999 | Penn et al. | 6,254,593 | B1 * | 7/2001 | Wilson ....................... 623/1.11 |
| 5,907,893 | A | 6/1999 | Zadno-Azizi et al. | 6,258,073 | B1 | 7/2001 | Mauch |
| 5,913,895 | A | 6/1999 | Burpee et al. | 6,258,099 | B1 | 7/2001 | Mareiro et al. |
| 5,913,897 | A | 6/1999 | Corso, Jr. et al. | 6,258,115 | B1 * | 7/2001 | Dubrul ........................ 606/200 |
| 5,921,958 | A | 7/1999 | Ressemann et al. | 6,258,116 | B1 | 7/2001 | Hojeibane |
| 5,922,020 | A | 7/1999 | Klein et al. | 6,258,121 | B1 | 7/2001 | Yang et al. |
| 5,928,248 | A | 7/1999 | Acker | 6,261,273 | B1 | 7/2001 | Ruiz |
| 5,938,682 | A | 8/1999 | Hojeibane et al. | 6,261,305 | B1 | 7/2001 | Marotta et al. |
| 5,938,696 | A | 8/1999 | Goicoechea et al. | 6,261,316 | B1 * | 7/2001 | Shaolian et al. ............ 623/1.11 |
| 5,948,016 | A | 9/1999 | Jang | 6,261,319 | B1 | 7/2001 | Kveen et al. |
| 5,951,599 | A | 9/1999 | McCrory | 6,264,662 | B1 * | 7/2001 | Lauterjung .................. 606/108 |
| 5,961,548 | A | 10/1999 | Shmulewitz | 6,264,682 | B1 | 7/2001 | Wilson et al. |
| 5,967,986 | A | 10/1999 | Cimochowski et al. | 6,264,686 | B1 * | 7/2001 | Rieu et al. .................. 623/1.16 |
| 5,972,017 | A * | 10/1999 | Berg et al. .................. 606/198 | 6,273,911 | B1 | 8/2001 | Cox et al. |
| 5,972,018 | A | 10/1999 | Israel et al. | 6,273,913 | B1 | 8/2001 | Wright et al. |
| 6,007,517 | A | 12/1999 | Anderson | 6,287,314 | B1 | 9/2001 | Lee et al. |
| 6,013,054 | A | 1/2000 | Jiun Yan | 6,290,673 | B1 | 9/2001 | Shanley |
| 6,013,091 | A | 1/2000 | Ley et al. | 6,293,967 | B1 | 9/2001 | Shanley |
| 6,017,324 | A * | 1/2000 | Tu et al. ................. 604/103.07 | 6,293,968 | B1 | 9/2001 | Taheri ........................ 623/1.15 |
| 6,017,363 | A | 1/2000 | Hojeibane | 6,299,634 | B1 | 10/2001 | Bergeron |
| 6,030,414 | A | 2/2000 | Taheri | 6,302,906 | B1 | 10/2001 | Goicoechea et al. |
| 6,033,434 | A | 3/2000 | Borghi | 6,309,412 | B1 | 10/2001 | Lau et al. |
| 6,033,435 | A | 3/2000 | Penn et al. | 6,309,414 | B1 | 10/2001 | Rolando et al. |
| 6,036,682 | A | 3/2000 | Lange et al. | 6,312,459 | B1 | 11/2001 | Huang et al. |

| | | | |
|---|---|---|---|
| 6,325,821 B1 | 12/2001 | Gaschino et al. | |
| 6,325,822 B1 * | 12/2001 | Chouinard et al. ......... 623/1.15 | |
| 6,325,826 B1 * | 12/2001 | Vardi et al. ................ 623/1.35 | |
| 6,334,864 B1 * | 1/2002 | Amplatz et al. ............. 606/200 | |
| 6,334,870 B1 | 1/2002 | Ehr et al. | |
| 6,346,089 B1 | 2/2002 | Dibie | |
| 6,355,060 B1 * | 3/2002 | Lenker et al. ............... 623/1.34 | |
| 6,361,544 B1 | 3/2002 | Wilson et al. | |
| 6,361,555 B1 | 3/2002 | Wilson | |
| 6,383,213 B2 * | 5/2002 | Wilson et al. ............... 623/1.11 | |
| 6,383,215 B1 | 5/2002 | Sass | |
| 6,387,120 B2 | 5/2002 | Wilson et al. | |
| 6,395,018 B1 | 5/2002 | Castaneda | |
| 6,398,792 B1 | 6/2002 | O'Connor | |
| 6,398,804 B1 | 6/2002 | Spielberg | |
| 6,428,570 B1 | 8/2002 | Globerman | |
| 6,432,133 B1 | 8/2002 | Lau et al. | |
| 6,436,104 B2 | 8/2002 | Hojeibane | |
| 6,436,134 B2 | 8/2002 | Richter et al. | |
| 6,478,816 B1 | 11/2002 | Kveen et al. | |
| 6,482,211 B1 | 11/2002 | Choi | |
| 6,485,511 B2 | 11/2002 | Lau et al. | |
| 6,494,905 B1 | 12/2002 | Zedler et al. | |
| 6,508,836 B2 * | 1/2003 | Wilson et al. ............... 623/1.35 | |
| 6,511,504 B1 | 1/2003 | Lau et al. | |
| 6,511,505 B2 | 1/2003 | Xoc et al. | |
| 6,517,558 B2 * | 2/2003 | Gittings et al. ............... 606/153 | |
| 6,520,988 B1 * | 2/2003 | Colombo et al. ........... 623/1.35 | |
| 6,527,799 B2 | 3/2003 | Shanley | |
| 6,540,719 B2 | 4/2003 | Bigus et al. | |
| 6,540,779 B2 | 4/2003 | Richter et al. | |
| 6,572,647 B1 | 6/2003 | Supper et al. | |
| 6,579,309 B1 | 6/2003 | Loos et al. | |
| 6,579,312 B2 | 6/2003 | Wilson et al. | |
| 6,582,394 B1 | 6/2003 | Reiss et al. | |
| 6,582,459 B1 | 6/2003 | Lau et al. | |
| 6,596,020 B2 * | 7/2003 | Vardi et al. ................ 623/1.11 | |
| 6,596,022 B2 | 7/2003 | Lau et al. | |
| 6,599,316 B2 * | 7/2003 | Vardi et al. ................ 623/1.15 | |
| 6,645,242 B1 * | 11/2003 | Quinn ....................... 623/1.16 | |
| 6,689,156 B1 * | 2/2004 | Davidson et al. ........... 623/1.11 | |
| 6,692,483 B2 * | 2/2004 | Vardi et al. ................ 604/529 | |
| 6,695,877 B2 * | 2/2004 | Brucker et al. ............. 623/1.16 | |
| 6,706,062 B2 * | 3/2004 | Vardi et al. ................ 623/1.15 | |
| 6,749,628 B1 * | 6/2004 | Callol et al. ............... 623/1.15 | |
| 6,776,793 B2 * | 8/2004 | Brown et al. ............... 623/1.15 | |
| 6,811,566 B1 | 11/2004 | Penn et al. .................. 623/1.15 | |
| 6,835,203 B1 * | 12/2004 | Vardi et al. ................ 623/1.34 | |
| 6,858,038 B2 * | 2/2005 | Heuser ....................... 623/1.35 | |
| 6,884,258 B2 * | 4/2005 | Vardi et al. ................ 623/1.11 | |
| 6,896,699 B2 * | 5/2005 | Wilson et al. ............... 623/1.35 | |
| 6,932,837 B2 * | 8/2005 | Amplatz et al. ............. 623/1.15 | |
| 6,955,687 B2 * | 10/2005 | Richter et al. ............... 623/1.35 | |
| 6,955,688 B2 * | 10/2005 | Wilson et al. ............... 623/1.35 | |
| 6,962,602 B2 * | 11/2005 | Vardi et al. ................ 623/1.11 | |
| 7,018,400 B2 * | 3/2006 | Lashinski et al. ........... 623/1.11 | |
| 7,056,323 B2 | 6/2006 | Mareiro et al. ............... 606/108 | |
| 7,060,091 B2 | 6/2006 | Killion et al. ............... 623/1.15 | |
| 7,118,593 B2 * | 10/2006 | Davidson et al. ........... 623/1.15 | |
| 7,678,142 B2 * | 3/2010 | Vardi et al. ................ 623/1.35 | |
| 2001/0003161 A1 * | 6/2001 | Vardi et al. ................ 623/1.11 | |
| 2001/0004706 A1 * | 6/2001 | Hojeibane ................... 623/1.11 | |
| 2001/0004707 A1 * | 6/2001 | Dereume et al. ............. 623/1.16 | |
| 2001/0012927 A1 | 8/2001 | Mauch | |
| 2001/0016766 A1 * | 8/2001 | Vardi et al. ................ 623/1.11 | |
| 2001/0016767 A1 | 8/2001 | Wilson et al. | |
| 2001/0016768 A1 | 8/2001 | Wilson et al. | |
| 2001/0025195 A1 * | 9/2001 | Shaolian et al. ........... 623/1.13 | |
| 2001/0027291 A1 | 10/2001 | Shanley | |
| 2001/0027338 A1 | 10/2001 | Greenberg | |
| 2001/0037116 A1 | 11/2001 | Wilson et al. | |
| 2001/0037138 A1 | 11/2001 | Wilson et al. | |
| 2001/0037146 A1 | 11/2001 | Lau et al. | |
| 2001/0037147 A1 | 11/2001 | Lau et al. | |
| 2001/0039395 A1 | 11/2001 | Mareiro et al. | |
| 2001/0039448 A1 | 11/2001 | Dibie | |
| 2001/0047201 A1 | 11/2001 | Cox et al. | |
| 2001/0049552 A1 | 12/2001 | Richter et al. | |
| 2001/0056297 A1 | 12/2001 | Hojeibane | |
| 2002/0013618 A1 | 1/2002 | Marotta et al. | |
| 2002/0013619 A1 | 1/2002 | Shanley | |
| 2002/0022874 A1 | 2/2002 | Wilson | |
| 2002/0026232 A1 | 2/2002 | Marotta et al. | |
| 2002/0032478 A1 | 3/2002 | Boekstegers et al. | |
| 2002/0035392 A1 | 3/2002 | Wilson | |
| 2002/0042650 A1 | 4/2002 | Vardi et al. | |
| 2002/0052648 A1 | 5/2002 | McGuckin, Jr. et al. | |
| 2002/0058990 A1 | 5/2002 | Jang | |
| 2002/0072790 A1 * | 6/2002 | McGuckin et al. ......... 623/1.12 | |
| 2002/0107564 A1 | 8/2002 | Cox et al. | |
| 2002/0111675 A1 | 8/2002 | Wilson | |
| 2002/0123790 A1 | 9/2002 | White et al. | |
| 2002/0123797 A1 | 9/2002 | Majercak | |
| 2002/0123798 A1 | 9/2002 | Burgermeister | |
| 2002/0151959 A1 | 10/2002 | Von Oepen | |
| 2002/0156516 A1 | 10/2002 | Vardi et al. | |
| 2002/0156517 A1 | 10/2002 | Perouse | |
| 2002/0165604 A1 | 11/2002 | Shanley | |
| 2002/0173835 A1 | 11/2002 | Bourang et al. | |
| 2002/0173840 A1 | 11/2002 | Brucker et al. | |
| 2002/0177892 A1 | 11/2002 | Globerman | |
| 2002/0183763 A1 | 12/2002 | Callol et al. | |
| 2002/0193872 A1 | 12/2002 | Trout, III et al. | |
| 2002/0193873 A1 | 12/2002 | Brucker et al. | |
| 2003/0004535 A1 | 1/2003 | Musbach et al. | |
| 2003/0009209 A1 | 1/2003 | Hojeibane | |
| 2003/0009214 A1 | 1/2003 | Shanley | |
| 2003/0014102 A1 | 1/2003 | Hong et al. | |
| 2003/0023301 A1 | 1/2003 | Cox et al. | |
| 2003/0028233 A1 * | 2/2003 | Vardi et al. ................ 623/1.11 | |
| 2003/0050688 A1 | 3/2003 | Fischell et al. | |
| 2003/0055378 A1 | 3/2003 | Wang et al. ............. 604/103.07 | |
| 2003/0055483 A1 * | 3/2003 | Gumm ..................... 623/1.11 | |
| 2003/0074047 A1 | 4/2003 | Richter | |
| 2003/0093109 A1 | 5/2003 | Mauch | |
| 2003/0097169 A1 * | 5/2003 | Brucker et al. ............. 623/1.11 | |
| 2003/0114912 A1 | 6/2003 | Sequin et al. | |
| 2003/0114915 A1 | 6/2003 | Mareiro et al. | |
| 2003/0125791 A1 | 7/2003 | Sequin et al. | |
| 2003/0125799 A1 | 7/2003 | Limon | |
| 2003/0125802 A1 | 7/2003 | Callol et al. | |
| 2003/0135259 A1 | 7/2003 | Simso ....................... 623/1.12 | |
| 2003/0181923 A1 | 9/2003 | Vardi ........................ 606/108 | |
| 2003/0195606 A1 | 10/2003 | Davidson et al. ........... 623/1.11 | |
| 2004/0006381 A1 * | 1/2004 | Sequin et al. ............... 623/1.12 | |
| 2004/0015227 A1 | 1/2004 | Vardi et al. | |
| 2004/0044396 A1 * | 3/2004 | Clerc et al. ................ 623/1.13 | |
| 2004/0059406 A1 * | 3/2004 | Cully et al. ................ 623/1.11 | |
| 2004/0088007 A1 * | 5/2004 | Eidenschink ................... 607/1 | |
| 2004/0117003 A1 * | 6/2004 | Ouriel et al. ............... 623/1.35 | |
| 2004/0133268 A1 * | 7/2004 | Davidson et al. ........... 623/1.35 | |
| 2004/0138732 A1 * | 7/2004 | Suhr et al. .................. 623/1.11 | |
| 2004/0138737 A1 * | 7/2004 | Davidson et al. ........... 623/1.35 | |
| 2004/0148006 A1 * | 7/2004 | Davidson et al. ........... 623/1.11 | |
| 2004/0172121 A1 * | 9/2004 | Eidenschink et al. ........ 623/1.11 | |
| 2004/0186560 A1 | 9/2004 | Alt ............................. 623/1.35 | |
| 2004/0225345 A1 | 11/2004 | Fischell et al. ............. 623/1.11 | |
| 2004/0267352 A1 * | 12/2004 | Davidson et al. ........... 623/1.15 | |
| 2005/0004656 A1 | 1/2005 | Das ........................... 623/1.16 | |
| 2005/0010278 A1 * | 1/2005 | Vardi et al. ................ 623/1.15 | |
| 2005/0015108 A1 * | 1/2005 | Williams et al. ............ 606/194 | |
| 2005/0015135 A1 | 1/2005 | Shanley ..................... 623/1.11 | |
| 2005/0060027 A1 * | 3/2005 | Khenansho et al. ........ 623/1.35 | |
| 2005/0096726 A1 | 5/2005 | Sequin et al. ............... 623/1.12 | |
| 2005/0102021 A1 * | 5/2005 | Osborne ..................... 623/1.13 | |
| 2005/0102023 A1 * | 5/2005 | Yadin et al. ................ 623/1.15 | |

| | | | |
|---|---|---|---|
| 2005/0119731 A1 | 6/2005 | Brucker et al. ............. 623/1.35 |
| 2005/0125076 A1 | 6/2005 | Ginn ....................... 623/23.65 |
| 2005/0131526 A1* | 6/2005 | Wong ........................ 623/1.15 |
| 2005/0149161 A1* | 7/2005 | Eidenschink et al. ........ 623/1.11 |
| 2005/0154442 A1* | 7/2005 | Eidenschink et al. ........ 623/1.11 |
| 2005/0154444 A1* | 7/2005 | Quadri ....................... 623/1.13 |
| 2005/0183259 A1* | 8/2005 | Eidenschink et al. ........... 29/508 |
| 2005/0209673 A1* | 9/2005 | Shaked ....................... 623/1.11 |
| 2005/0228483 A1 | 10/2005 | Kaplan et al. .............. 623/1.15 |
| 2006/0036315 A1 | 2/2006 | Yadin et al. ................ 623/1.35 |
| 2006/0041303 A1* | 2/2006 | Israel ........................ 623/1.11 |
| 2006/0079956 A1 | 4/2006 | Eigler et al. ............... 623/1.35 |
| 2006/0173528 A1 | 8/2006 | Feld et al. .................. 623/1.15 |
| 2007/0073376 A1 | 3/2007 | Krolik et al. ............... 623/1.11 |

FOREIGN PATENT DOCUMENTS

| | | |
|---|---|---|
| CA | 2220864 | 7/1999 |
| DE | 9014845 U1 | 2/1991 |
| DE | 29701883 | 5/1997 |
| EP | 0479730 | 10/1991 |
| EP | 0621017 | 4/1994 |
| EP | 0621017 A1 * | 4/1994 |
| EP | 0621017 A1 * | 10/1994 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 0897698 | 6/2004 |
| EP | 1157674 B1 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 8806026 | 8/1988 |
| WO | 9013332 | 11/1990 |
| WO | 9112779 | 9/1991 |
| WO | 9219308 | 11/1992 |
| WO | 9521592 | 8/1995 |
| WO | 96/29955 | 10/1996 |
| WO | 96/34580 | 11/1996 |
| WO | 9641592 | 12/1996 |
| WO | 97/07752 | 3/1997 |
| WO | 97/15346 | 5/1997 |
| WO | 9716217 | 5/1997 |
| WO | 9709946 | 6/1997 |
| WO | 9726936 | 7/1997 |
| WO | 9733532 | 9/1997 |
| WO | 9741803 | 11/1997 |
| WO | 97/46174 | 12/1997 |
| WO | 9745073 | 12/1997 |
| WO | 9817204 | 4/1998 |
| WO | 9819628 | 5/1998 |
| WO | 9835634 | 8/1998 |
| WO | 9836709 | 8/1998 |
| WO | 9837833 | 9/1998 |
| WO | 98/47447 | 10/1998 |
| WO | 9844871 | 10/1998 |
| WO | 98/48879 | 11/1998 |
| WO | 9848733 | 11/1998 |
| WO | 9852497 | 11/1998 |
| WO | 99/03426 | 1/1999 |
| WO | 99/04726 | 2/1999 |
| WO | 99/15109 | 4/1999 |
| WO | 9915103 | 4/1999 |
| WO | 9917680 | 4/1999 |
| WO | 99/24104 | 5/1999 |
| WO | 99/36015 | 7/1999 |
| WO | 9934749 | 7/1999 |
| WO | 9936002 | 7/1999 |
| WO | 9939661 | 8/1999 |
| WO | 99/44539 | 9/1999 |
| WO | 99/56661 | 11/1999 |
| WO | 9958059 | 11/1999 |
| WO | 9965419 | 12/1999 |
| WO | 0000104 | 1/2000 |
| WO | 00/07523 | 2/2000 |
| WO | 00/10489 | 3/2000 |
| WO | 00/16719 | 3/2000 |
| WO | 0012166 | 3/2000 |
| WO | 0013613 | 3/2000 |
| WO | 00/27307 | 5/2000 |
| WO | 00/27463 | 5/2000 |
| WO | 00/28922 | 5/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 0053122 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 0074595 | 12/2000 |
| WO | 0121095 | 3/2001 |
| WO | 0121109 | 3/2001 |
| WO | 0121244 | 3/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45594 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/70294 | 9/2001 |
| WO | 0170299 | 9/2001 |
| WO | 01/74273 | 10/2001 |
| WO | 01/89409 | 11/2001 |
| WO | 02/00138 | 1/2002 |
| WO | 02/053066 | 7/2002 |
| WO | 02068012 | 9/2002 |
| WO | 02076333 | 10/2002 |
| WO | 02094336 | 11/2002 |
| WO | 03/007842 | 1/2003 |
| WO | 03055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |

| WO | 2005/014077 | 2/2005 |
| WO | 2006/028925 | 3/2006 |

OTHER PUBLICATIONS

U.S. Appl. No. 09/614,472, filed Jul. 11, 2000, Davidson et al.

U.S. Appl. No. 09/325,996, filed Jun. 4, 1999, Vardi et al.

Serruys, M.D., Patrick W., "A Comparison of Balloon-Expandable-Stent Implantation with Balloon Angioplasty In Patients with Coronary Artery Disease," The New England Journal of Medicine, vol. 331:8, pp. 489-495 (Aug. 25, 1994).

Chevalier, M.D., Bernard, "Placement of Coronary Stents in Bifurcation Lesions by the "Culotte" Technique," The American Journal of Cardiology, vol. 82, pp. 943-949 (Oct. 15, 1998).

Fischmann, M.D., David L., "A Randomized Comparison of Coronary-Stent Placement and Balloon Angioplasty in the Treatment of Coronary Artery Disease," The New England Journal of Medicine, vol. 331:8, pp. 496-501 (Aug. 25, 1994).

Nakamura M.D., Shigeru, "Techniques for Palmaz-Schatz Stent Deployment in Lesions with a Large Side Branch," Catheterization and Cardiovascular Diagnosis, vol. 34, pp. 353-361 (1995).

Caputo, Ronald P., "Stent Jail: A Minimum-Security Prison," The American Journal of Cardiology, vol. 77, pp. 1226-1230 (Jun. 1, 1996).

Colombo, M.D., Antonio, ""Kissing" Stent for Bifurcational Coronary Lesion," Catheterization and Cardiovascular Diagnosis, vol. 30, pp. 327-330 (Dec. 1993).

Carrie, M.D., Didier, ""T"-Shaped Stent Placement: A Technique for the Treatment of Dissected Bifurcation Lesions," Catheterization and Cardiovascular Diagnosis, vol. 37, pp. 311-313 (Mar. 1996).

Katoh, M.D., Osamu, "New Double Wire Technique to Stent Ostial Lesions," Catheterization and Cardiovascular Diagnosis, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," American Heart Journal, vol. 127:6, pp. 1600-1607 (Jun. 1994).

Dichek, M.D., David A., "Seeding of Intravascular Stents with Genetically Engineered Endothelial Cells," Circulation, vol. 80:5, pp. 1347-1353 (Nov. 1989).

Yamashita, M.D.,PhD., Takehiro, "Bifurcation Lesions: Two Stents Versus One Stent—Immediate and Follow-up Results," Journal of the American College of Cardiology, vol. 35:5, pp. 1145-1151 (Apr. 2000).

Satler, M.D., Lowell F., "Bifurcation Disease: To Treat or Not to Treat," Catheterization and Cardiovascular Interventions, vol. 50, pp. 411-412 (2000).

SCIMED Life Systems, Inc.—TRIO™ 14 PTCA Catheter, Re-engineering Over-the-Wire Balloon Technology, Company Brochure, © 1994.

* cited by examiner

EXTENDIBLE STENT APPARATUS

This Application is a continuation of U.S. patent application Ser. No. 10/440,401, filed May 19, 2003, now U.S. Pat. No. 7,766,955; which is a continuation of U.S. patent application Ser. No. 09/750,372, filed Dec. 27, 2000, now U.S. Pat. No. 6,599,316; which is a continuation-in-part of application Ser. No. 09/007,265, filed on Jan. 14, 1998, now U.S. Pat. No. 6,210,429; which is a continuation-in-part of U.S. patent application Ser. No. 08/744,002, filed on Nov. 4, 1996, now abandoned, the disclosures of which are hereby incorporated by reference herein in their entirety.

BACKGROUND

A type of endoprosthesis device, commonly referred to as a stent, may be placed or implanted within a vein, artery or other tubular body organ for treating occlusions, stenoses, or aneurysms of a vessel by reinforcing the wall of the vessel or by expanding the vessel. Stents have been used to treat dissections in blood vessel walls caused by balloon angioplasty of the coronary arteries as well as peripheral arteries and to improve angioplasty results by preventing elastic recoil and remodeling of the vessel wall. Two randomized multicenter trials have recently shown a lower restenosis rate in stent treated coronary arteries compared with balloon angioplasty alone (Serruys, P W et. al. New England Journal of Medicine 331: 489-495, 1994, Fischman, D L et. al. New England Journal of Medicine 331: 496-501, 1994). Stents have been successfully implanted in the urinary tract, the bile duct, the esophagus and the tracheo-bronchial tree to reinforce those body organs, as well as implanted into the neurovascular, peripheral vascular, coronary, cardiac, and renal systems, among others. The term "stent" as used in this application is a device which is intraluminally implanted within bodily vessels to reinforce collapsing, dissected, partially occluded, weakened, diseased or abnormally dilated or small segments of a vessel wall.

One of the drawbacks of conventional stents is that they are generally produced in a straight tubular configuration. The use of such stents to treat diseased vessels at or near a bifurcation (branch point) of a vessel may create a risk of compromising the degree of patency of the primary vessel and/or its branches, or the bifurcation point and also limits the ability to insert a second stent into the side branch if the result of treatment of the primary, or main, vessel is suboptimal. Suboptimal results may occur as a result of several mechanisms, such as displacing diseased tissue, plaque shifting, vessel spasm, dissection with or without intimal flaps, thrombosis, and embolism.

The risk of branch compromise is increased generally in two anatomical situations. First, a side branch may be compromised when there is a stenosis in the origin of the side branch. Second, when there is an eccentric lesion at the bifurcation site, asymmetric expansion can cause either plaque shifting or dissection at the side branch origin. There are reports of attempts to solve this problem by inserting a balloon into the side branch through the struts of a stent deployed in the main branch spanning the bifurcation point; however, this technique carries the risk of balloon entrapment and other major complications (Nakamura, S. et al., Catheterization and Cardiovascular Diagnosis 34: 353-361 (1995)). Moreover, adequate dilation of the side branch is limited by elastic recoil of the origin of the side branch. In addition, insertion of a traditional stent into a main vessel spanning the bifurcation point may pose a limitation to blood flow and access to the side branch vessel. The term "stent jail" is often used to describe this concept. In this regard, the tubular slotted hinged design of the Palmaz-Schatz intracoronary stent, in particular, is felt to be unfavorable for lesions with a large side branch and is generally believed to pose a higher risk of side branch vessel entrapment where the stent prevents or limits access to the side branch. Id.

One common procedure for intraluminally implanting a stent is to first open the relevant region of the vessel with a balloon catheter and then place the stent in a position that bridges the treated portion of the vessel in order to prevent elastic recoil and restenosis of that segment. The angioplasty of the bifurcation lesion has traditionally been performed using the "kissing" balloon technique where two guidewires and two balloons are inserted, one into the main branch and the other into the side branch Stent placement in this situation requires the removal of the guidewire from the side branch and reinsertion through the stent struts, followed by the insertion of a balloon through the struts of the stent along the guidewire. The first removal of the guidewire poses the risk of occlusion of the side branch during the deployment of the stent in the main branch.

Prior art patents refer to the construction and design of both the stent as well as the apparatus for positioning the stent within the vessel. One representative patent to Chaudhury, U.S. Pat. No. 4,140,126, discloses a technique for positioning an elongated cylindrical stent at a region of an aneurysm to avoid catastrophic failure of the blood vessel wall. The '126 patent discloses a cylinder that expands to its implanted configuration after insertion with the aid of a catheter. Dotter, U.S. Pat. No. 4,503,569, discloses a spring stent which expands to an implanted configuration with a change in temperature. The spring stent is implanted in a coiled orientation and is then heated to cause the spring to expand. Palmaz, U.S. Pat. No. 4,733,665, discloses a number of stent configurations for implantation with the aid of a catheter. The catheter includes a mechanism for mounting and retaining a stent, preferably on an inflatable portion of the catheter. The stents are implanted while imaged on a monitor. Once the stent is properly positioned, the catheter is expanded and the stent separated from the catheter body. The catheter can then be withdrawn from the subject, leaving the stent in place within the blood vessel. Palmaz, U.S. Pat. No. 4,739,762, discloses an expandable intraluminal graft. Schjeldahl et. al., U.S. Pat. No. 4,413,989, discloses a variety of balloon catheter constructions. Maginot, U.S. Pat. No. 5,456,712 and Maginot, U.S. Pat. No. 5,304,220 disclose a graft and stent assembly and a method of implantation where a stent is used to reinforce a graft that is surgically inserted into a blood vessel in order to bypass an occlusion. However, none of these patents relate to stents which are structurally adapted for the treatment of bifurcation lesions, or disclose a bifurcating stent apparatus.

Taheri, U.S. Pat. No. 4,872,874, Piplani et. al., U.S. Pat. No. 5,489,295, and Marin et al., U.S. Pat. No. 5,507,769, disclose bifurcating graft material which may be implanted using stents as anchors for the graft. However, bifurcated stents are not taught or disclosed, and the purpose of the stent as used in these inventions is simply to anchor the graft into the vessel wall. It does not reinforce the vessel wall, treat a lesion, or prevent restenosis after angioplasty.

MacGregor, U.S. Pat. No. 4,994,071, discloses a hinged bifurcating stent. In the 071' patent, in contrast to the present invention, there is a main stent with two additional stents attached at one end of the main stent, creating a single unit with a trunk attached at an end to two smaller stents. The two additional stents are permanently attached to the end of the trunk (and not the side, as in the present invention) and cannot be removed from the main stent. Thus, this invention may not be used to treat only one branch of a bifurcated vessel, is not appropriate for use when the branch vessel extends laterally from the side of a main vessel (as opposed to an end of a main vessel), and does not cover the origin of a bifurcated vessel or bifurcation lesion. In addition, studies with hinge-containing stents have shown that there is a high incidence of restenosis (tissue growth) at the hinge point that may cause narrowing or total occlusion of the vessel and thus compromise blood flow. Furthermore, this design has a relatively large size as compared to the present invention, which makes insertion into many smaller vessels difficult and poses a greatly increased risk of complications. Also, by having the two additional smaller stents connected to an end of the trunk stent, tracking into a wide-angle lateral side branch may be difficult and may carry the risk of dissection of the vessel wall. Furthermore, once the device of the '071 patent is implanted, it is impossible to exchange a branch stent should the need for a different stent size or repair of a branch stent arise.

Marcade, U.S. Pat. No. 5,676,696, discloses a bifurcated graft assembly used for 1 repairing abdominal aortic aneurysms, comprising a series of interlocked tubes, one of which comprises a fixed angle single bifurcated graft assembly. In contrast to the present invention, Marcade discloses a graft, not a stent, which may not be used to treat only one vessel of a bifurcation (leaving the untreated vessel free from all obstructions). In addition, and in contrast to the present invention, the one-piece bifurcated graft portion of Marcade is uniform in size and fixed in angle, and may not be used in a vessel bifurcation where the branch and the main vessels differ greatly in size. Also, the fixed angle will not provide as exact a fit as the variably-angled branched double-stent of the invention.

U.S. Pat. No. 5,653,743 to Martin discloses a bifurcated graft assembly for use in the hypogastric and iliac arteries. In addition to teaching grafts (which are used to replace diseased vessel material) and not stents (which, as used herein, reinforce existing vessels) Martin, in contrast to the present invention, discloses a side branch graft attached to the main graft as a single unit, requiring a larger profile than the subject stent. Martin also claims and discloses much larger component sizes and methods for implantation (appropriate for the hypograstric artery, to which Martin is limited) than are operable in smaller vessels, such as those of the cardiac, coronary, renal, peripheral vascular, gastrointestinal, pulmonary, urinary or neurovascular system, or brain vessels. In addition, Martin requires two vascular access sites (FIG. 3, elements 16 and 18), whereas the device of the present invention requires only one access site, creating less trauma to the patient.

U.S. Pat. No. 5,643,340 to Nunokowa discloses a synthetic vascular bypass graft in which a side branch graft extends outward from the side of a second portion of the graft unit. Nunokawa, however, discloses surgically implanted extraluminal grafts and not intraluminal stents deployed by catheterization, and is therefore unrelated to the subject of bifurcation lesions and stents, particularly stents used to intraluminally reinforce bifurcated vessels. In contrast to the present invention, Nunokawa is surgically implanted outside of the lumen of a vessel and in fact is used to bypass damaged regions of a vessel entirely. The present invention is used to reinforce the diseased region, and is intraluminally implanted directly into the diseased region. Additionally, and unlike the present invention, the Nunokawa device is surgically implanted and after surgical assembly of its components forms a single permanently attached unit, wherein the bifurcating stent devices of the invention are deployed intraluminally by catheter and do not require surgery or the suturing or attaching of parts of the invention to each other or to the body vessels, allowing for adaptation to varying branch vessel angles. Also, unlike the present invention, Nunokawa does not require visualization by x-ray or ultrasound, as the Nunokawa device is directly seen during surgery. Lastly, the Nunokawa device cannot be deployed using catheters, is not inserted intraluminally in a compressed state and expanded while inside a vessel, and has a much larger profile than the present invention.

In general, when treating a bifurcation lesion using commercially available stents, it is important to cover the origin of the branch because if left uncovered, this area is prone to restenosis. In order to cover the branch origin, conventional stents inserted into the branch must protrude into the lumen of the main artery or vessel from the branch (which may cause thrombosis, again compromising blood flow). Another frequent complication experienced when stenting bifurcated vessels is the narrowing or occlusion of the origin of a side branch spanned by a stent placed in the main branch. Additionally, placement of a stent into a main vessel where the stent partially or completely extends across the opening of a branch makes future access into such branch vessels difficult if not impossible. As a result, conventional stents are often placed into the branch close to the origin, but generally not covering the origin of the bifurcation.

Lastly, conventional stents are difficult to visualize during and after deployment, and in general are not readily imaged by using low-cost and easy methods such as x-ray or ultrasound imaging. While some prior art balloon catheters (and not stents) are "marked" at the proximal and distal ends of the balloon with imageable patches, few stents are currently available which are marked with, or which are at least partly constructed of, a material which is imageable by currently known imaging procedures commonly used when inserting the stents into a vessel, such as ultrasound or x-ray imaging. The invention described in this Application would not work with endoscopy as currently used as an imaging method due to size limitations, but future advances in limiting the size of endoscopic imaging devices may in the future make endoscopic imaging compatible with the stents of the invention.

Accordingly, there is a need for improved stent apparatuses, most particularly for applications within the cardiac, coronary, renal, peripheral vascular, gastrointestinal, pulmonary, urinary and neurovascular systems and the brain which 1) completely covers the bifurcation point of bifurcation vessels; 2) may be used to treat lesions in one branch of a bifurcation while preserving access to the other branch for future treatment; 3) allows for differential sizing of the stents in a bifurcated stent apparatus even after the main stent is implanted; 4) may be delivered intraluminally by catheter; 5) may be used to treat bifurcation lesions in a bifurcated vessel where the branch vessel extends from the side of the main vessel; and 6) is marked with, or at least partly constructed of, material which is imageable by commonly used intraluminal catheterization visualization techniques including but not limited to ultrasound or x-ray.

SUMMARY OF THE INVENTION

The present invention concerns novel stent apparatuses for use in treating lesions at or near the bifurcation point in bifurcated vessels. More particularly, the invention concerns a stent apparatus with at least one side opening which may further comprise an extendable stent portion inserted through the side opening and at least partly in registry with the wall of the side opening. As used herein, the term "vessel" means tubular tissue within the cardiac, coronary, renal, peripheral vascular, gastrointestinal, pulmonary, urinary and neurovascular systems and the brain. Devices constructed in accordance with the invention include, singularly or in combination, a main expandable stent comprising at least one substantially circular side opening located between its proximal and distal end openings, which side opening may further comprise a radially expandable portion extending laterally outward from the edges of the side opening; and an expandable branch stent comprising proximal and distal end openings and which may further comprise a contacting portion at its proximal end, and which may be constructed to form an angularly variable branched stent apparatus when inserted through a side opening of the main stent. The stents of the invention are marked with, or at least partially constructed of, a material which is imageable during intraluminal catheterization techniques, most preferably but not limited to ultrasound and x-ray.

The stent apparatuses of the invention offers significant and novel advantages over prior art stents in that the stents of the invention 1) can completely cover the bifurcation point of a branched vessel; 2) can accomodate main and branch stents of differing sizes, thus providing a better fit where the main and branch vessels are of different sizes or where the main and branch vessels are occluded to different degrees; 3) can fit branched vessels where the branch extends laterally from the side of the main vessel; 4) may be used to treat lesions in one branch of a bifurcation while preserving complete access to the other branch for future treatment; 5) may be delivered intraluminally by catheter; and 6) are marked with, or at least partly constructed of, material which is imageable by commonly used intraluminal catheterization visualization techniques including but not limited to ultrasound or x-ray, but not endoscopy.

Thus, it is an object of the present invention to provide both a double-stent apparatus and a single-stent apparatus, each of which may be used to cover the origin of a bifurcation in a branched vessel.

Another object of the invention is to provide a single-stent apparatus which may be used to treat only one branch of a bifurcation lesion while leaving access to the second branch unobstructed.

Additionally, it is an object of the invention to provide a stent apparatus which is itself imageable by methods commonly used during catheterization such as x-ray or ultrasound.

Yet another object of the invention is to provide a bifurcating double-stent device wherein the main stent and the branch stent or stents may be of different sizes.

Lastly, it is an important object of the invention to provide a stent apparatus which may be used to treat bifurcated vessels where the vessel bifurcation extends laterally from the side of the main vessel.

These objects and other object advantages and features of the invention will become better understood from the detailed description of the invention and the accompanying drawings.

BRIEF DESCRIPTION OF THE DRAWINGS

FIG. 6 is a schematic depiction of the stents of the invention at various points during deployment within a vessel.

Figure 1:
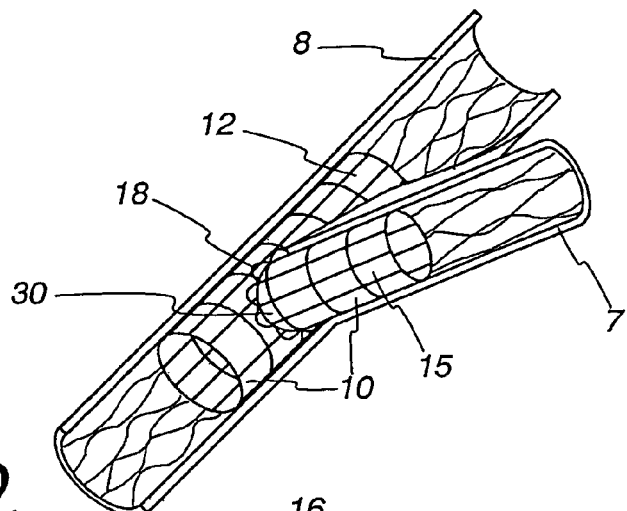
FIG. 1 is a schematic depiction of the double-stent apparatus of the present invention in which both the main stent and the branch stent are fully dilated.

The rectilinear matrices shown in the drawings are intended to show the shapes of the surfaces only, and do not illustrate the actual surface patterns or appearances of the stent apparatuses of the invention.

DESCRIPTION OF THE PREFERRED EMBODIMENTS

The bifurcating double-stent apparatus 10 of the present invention comprises a generally cylindrical main stent 12 and a generally cylindrical branch stent 15, which are shown as fully dilated in a subject main vessel 8 and a subject branch vessel 7, as illustrated in FIG. 1.

Figure 2:
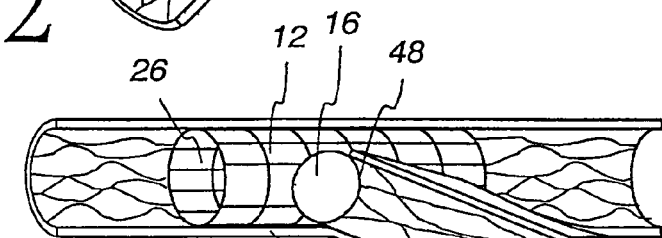
FIG. 2 is a schematic depiction of the main stent of the apparatus of the invention as deployed, with the side opening in registry with a vessel bifurcation point.

The main stent 12 contains at least one generally circular side opening 16 located between the proximal end 26 and the distal end 28 of the main stent 12 (FIG. 2), which opening is positioned over and in registry with the opening 48 of a branch vessel in a vessel bifurcation 50, as shown in FIG. 2. The stent 12 and the side opening are imaged during imaging procedures either by constructing the stent of imageable materials or by placing markers 56 at appropriate locations, such as around the perimeter of the side opening 16 in the main stent 12, and at the proximal end 26 and distal end 28 of the main stent, as illustrated in FIG. 4.

In some embodiments, the side opening 16 is symmetrical. In some embodiments, the side opening is oval. In some embodiments, a perimeter of the side opening 16 is continuously concave with respect to a centerpoint of the side opening 16. In some embodiments, the side opening 16 is closer to one end of the stent than the other. For example, in FIG. 4, the side opening 16 is closer to the distal end 28 than the proximal end 26.

Figure 4:
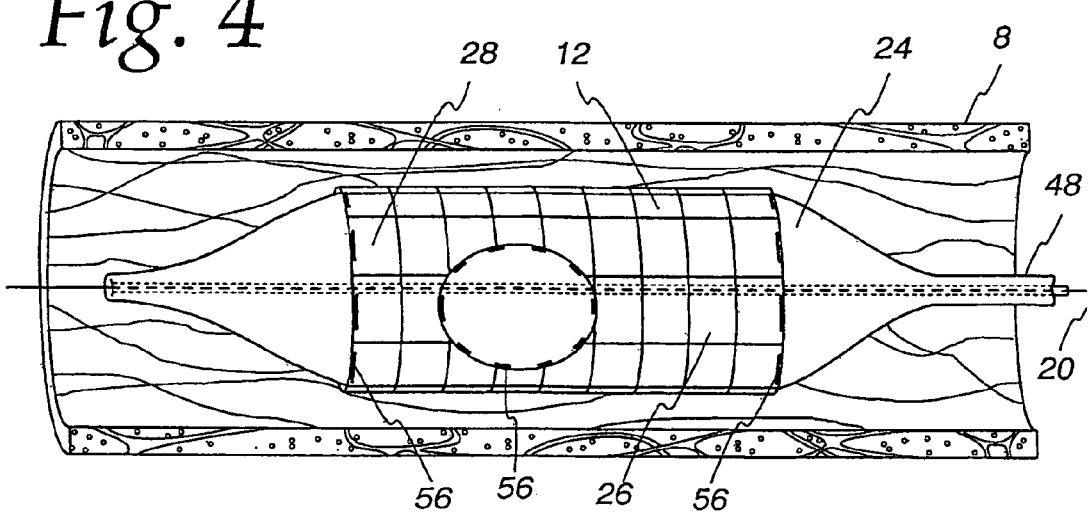
FIG. 4 is a schematic depiction of the main stent of the apparatus deployed within a subject vessel, after inflation of a balloon to expand the main stent to fit the walls of the subject vessel.

As shown in the embodiment of the invention illustrated in FIG. 4, a guidewire 20 is inserted into the vessel 8 prior to insertion of the main stent 12, and is used to guide the main stent 12 into position within the vessel 8. Prior to insertion and expansion, the main stent 12 is disposed around the distal end of a catheter 48 which may include an inflatable balloon 24. The main stent/catheter apparatus is then threaded onto the main guidewire 20 and into the vessel 8. The main stent 12 is radially expanded by inflation of the balloon 24 until it expands the walls of the vessel 8, and is thus affixed into place.

Figure 3:
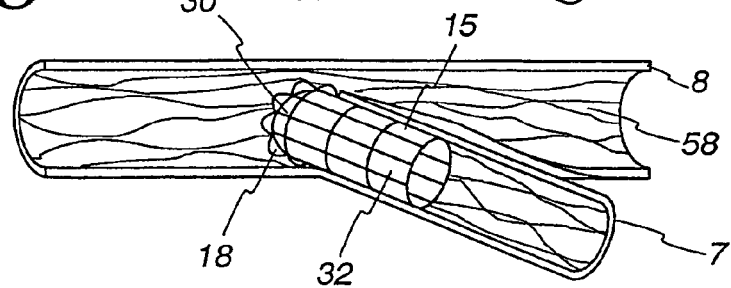
FIG. 3 is a schematic depiction of the branch stent of the apparatus as deployed, with the contacting portion fully expanded to contact the origin of the bifurcated vessel.

In a second embodiment of the invention, the branch stent apparatus 15 of the present invention comprises a generally cylindrical stent comprising a proximal end 30 and a distal end 32, as shown in FIG. 3. The proximal end 30 comprises a contacting portion, illustrated here as extended loops 18, which contacting portion, when expanded, is positioned within the lumen 58 of the main vessel 8 (FIG. 3) and at least partially contacting the perimeter of the side opening 16 of the main stent 12. FIG. 4 illustrates the positioning of the main stent 12 (without optional contacting portion) in the main vessel 8 as fully expanded by inflation of the balloon 24.

Figure 5:
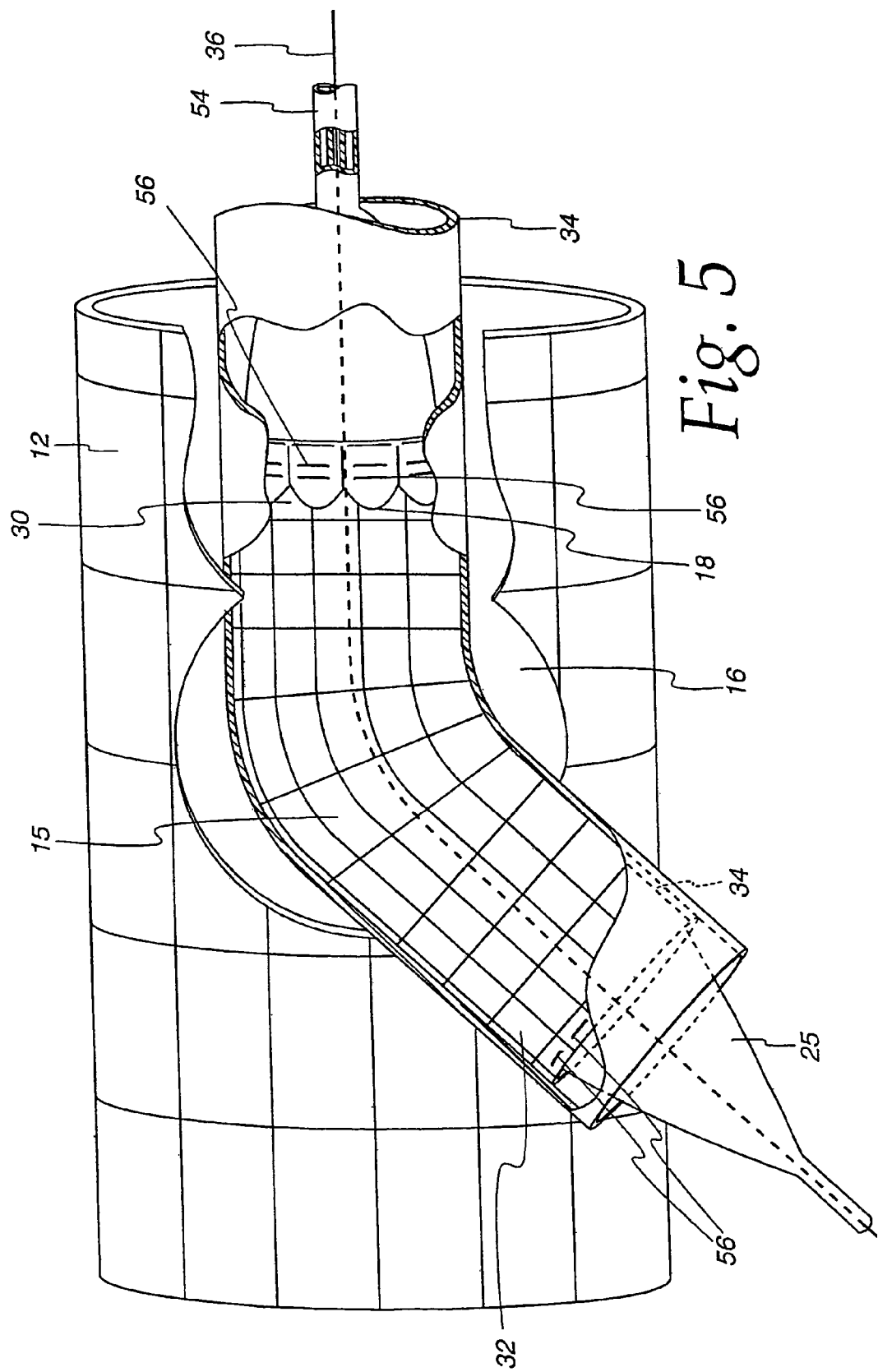
FIG. 5 is a schematic depiction of the double-stent bifurcating stent apparatus, where the main stent is deployed and showing the placement of the branch stent apparatus prior to full deployment of the branch stent.
Figure 7:
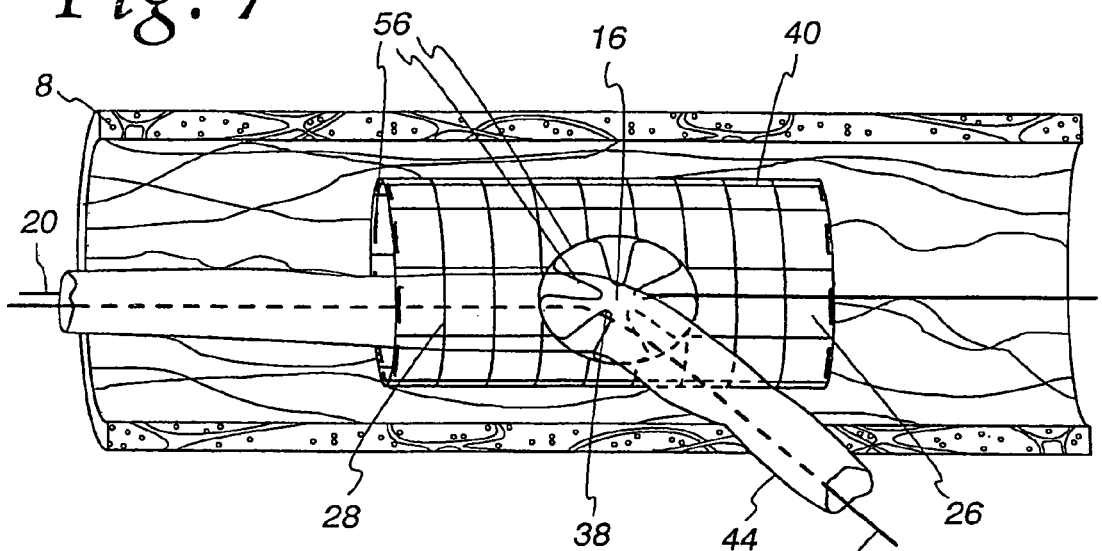
FIG. 7 is a schematic depiction of the main stent with optional expandable portion, prior to balloon expansion of the expandable portion.

As shown in the embodiments illustrated in FIGS. 4, 5 and 7, the ends of the main stent 12 and the expandable branch stent 15 and the contacting portion 18 are visible during insertion by placing imageable markers 56 around the ends of the main 12 and branch 15 stents and the contacting portion 18 and at the proximal end 30 and distal end 32 of the branch stent. Alternatively, the stent may be at least partially constructed of material which is imageable by methods including but not limited to ultrasound or x-ray imaging (but not endoscopic imaging).

As shown in yet another embodiment, the stents of the invention are combined to form a bifurcating double stent as illustrated in FIGS. 5 and 6. After insertion of the main stent as described above but prior to expansion of the main stent (FIG. 6a), the branch stent 15 is inserted through a side opening 16 of the main stent 12, a guidewire 36 and a stabilizing catheter 44 are inserted through the side opening 16 in the main stent 12, and into a branch vessel 7 (FIG. 6a). The stabilizing catheter 44 is used to place the side opening 16 in the main stent 12 over the bifurcation point 50 in the bifurcated vessels 7 and 8 (FIG. 6a). In the embodiment depicted here, the main stent is then deployed into position by inflation of the balloon 24 (FIG. 6b). During insertion and prior to dilation of the branch stent, the branch stent 15 is disposed around the distal end of a branch catheter 54 which may optionally include an inflatable balloon 25, and the contacting portion 18 of the branch stent 15 is held in a collapsed position by a protective sheath 34, as shown in FIG. 6c.

Figure 6A:
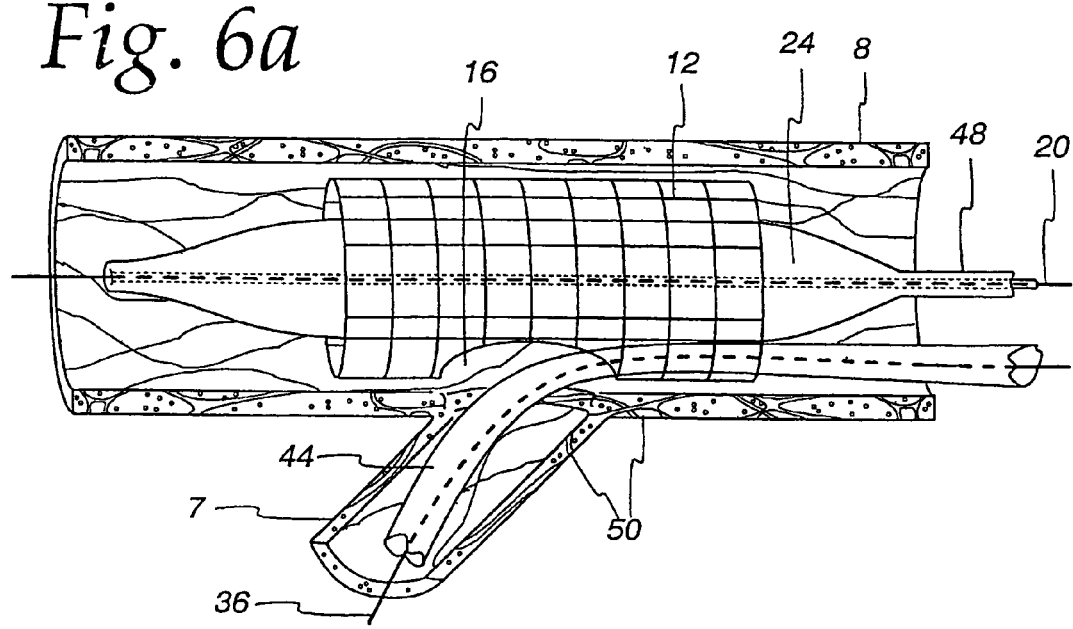
FIG. 6a depicts initial placement of the main stent of the bifurcating stent apparatus into the vessel, along with the insertion of a guidewire and stabilizing catheter for placement of the branch stent into the branch vessel of the subject.
Figure 6B:
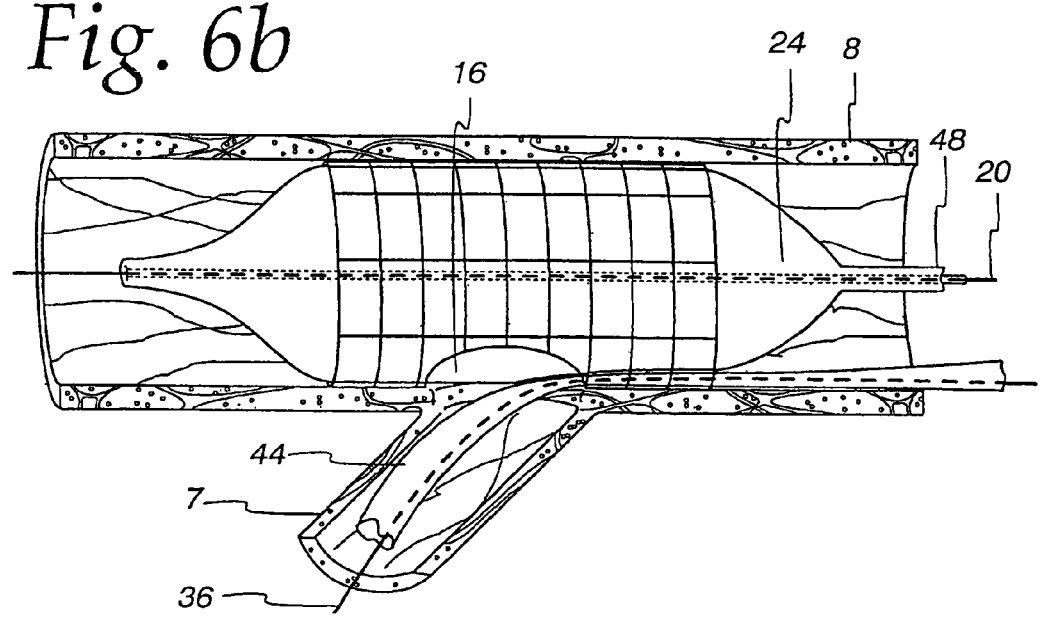
FIG. 6b is a schematic depiction showing the main stent of the invention expanded by balloon expansion.
Figure 6C:
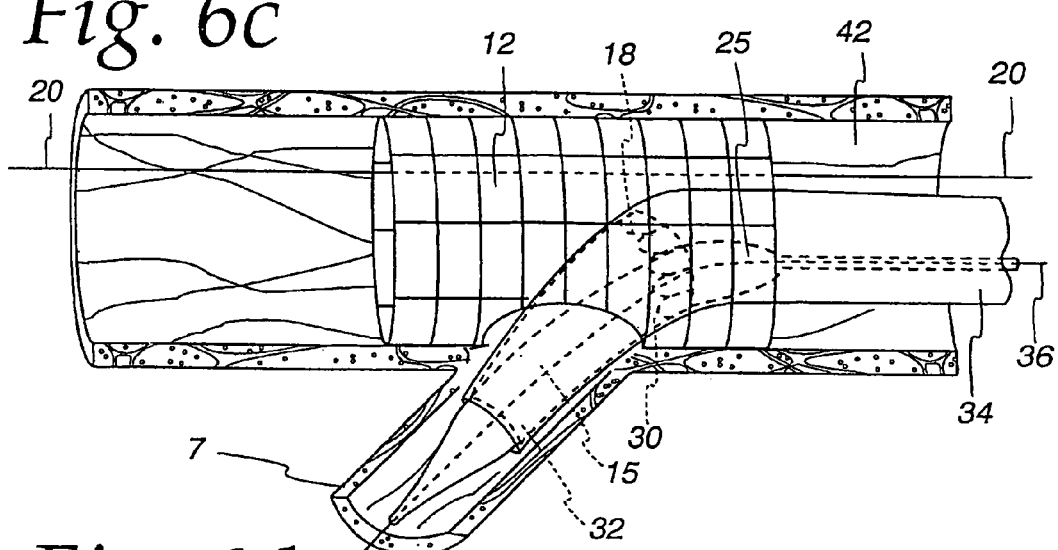
FIG. 6c is a schematic depiction of the deployment of the branch stent over the side branch guidewire, through one of the side openings in the main stent and into the branch vessel of the subject.
Figure 6D:
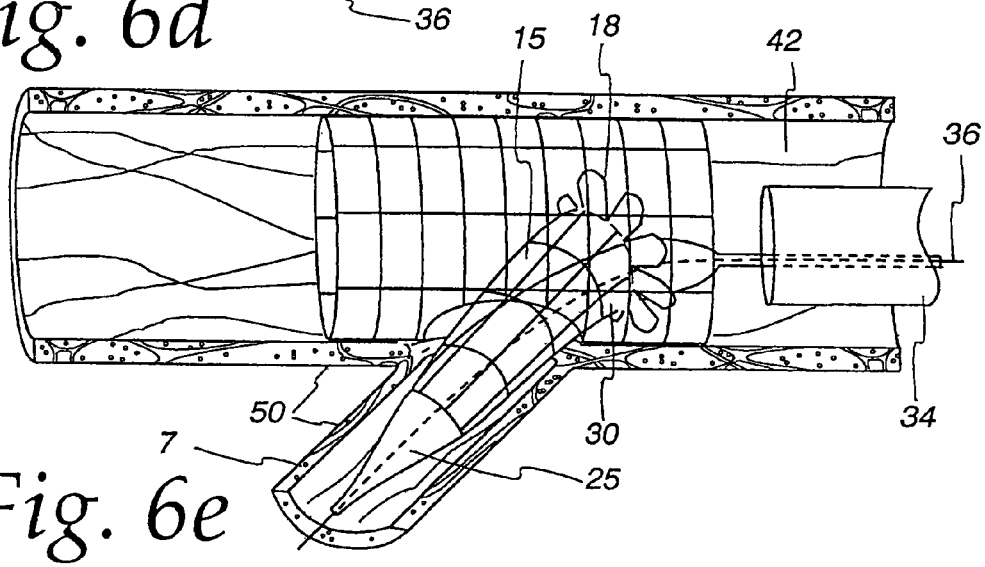
FIG. 6d is a schematic depiction of the removal of the protective sheath of the branch stent, allowing for full expansion of the contacting portion prior to final placement and deployment.
Figure 6E:
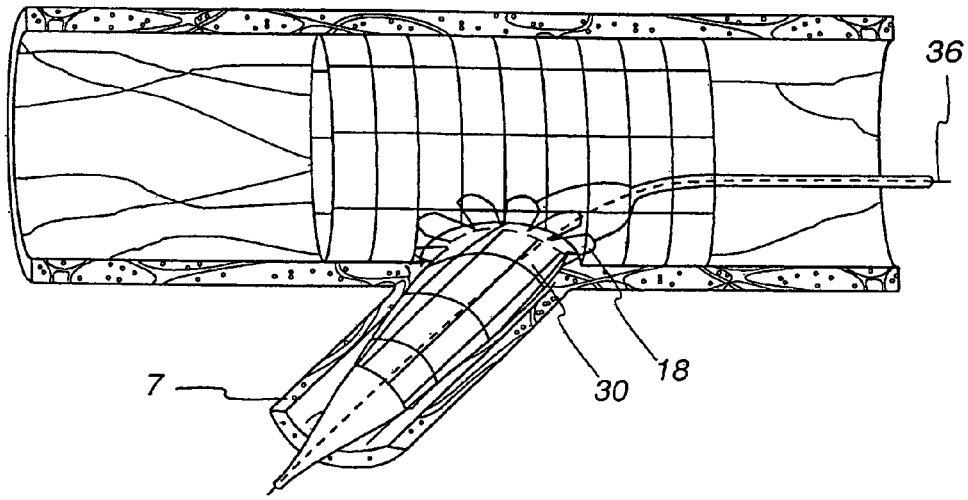
FIG. 6e is a schematic depiction of the compressed branch stent positioned into the branch by the catheter with the contacting portion at least partly contacting the side opening in the main stent, but prior to full expansion of the branch stent.
Figure 6F:
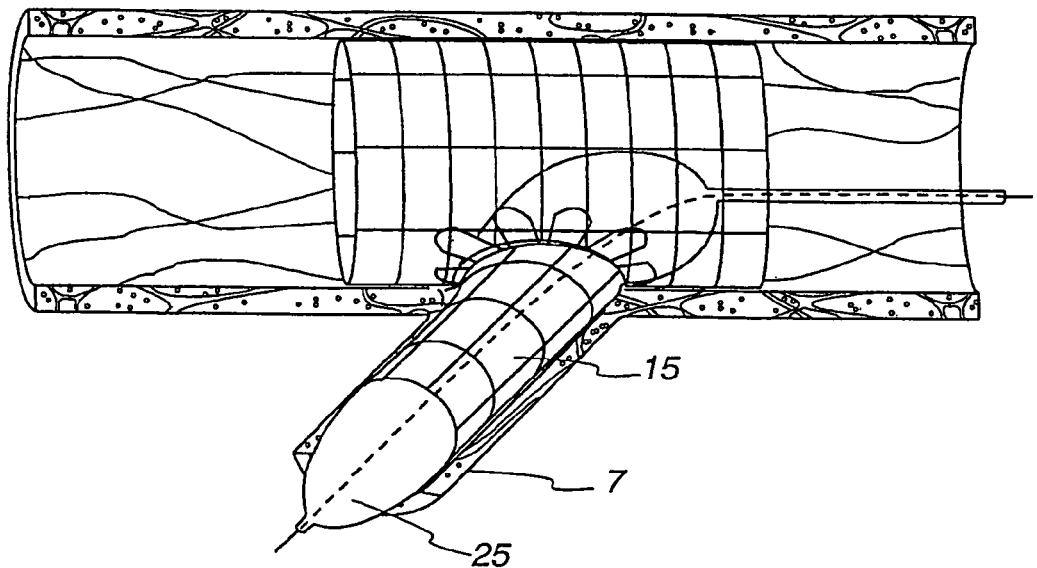
FIG. 6f is a schematic depiction of the fully expanded main stent and the fully positioned and expanded branch stent, where the branch stent is being dilated by inflation of a balloon.
Figure 6G:
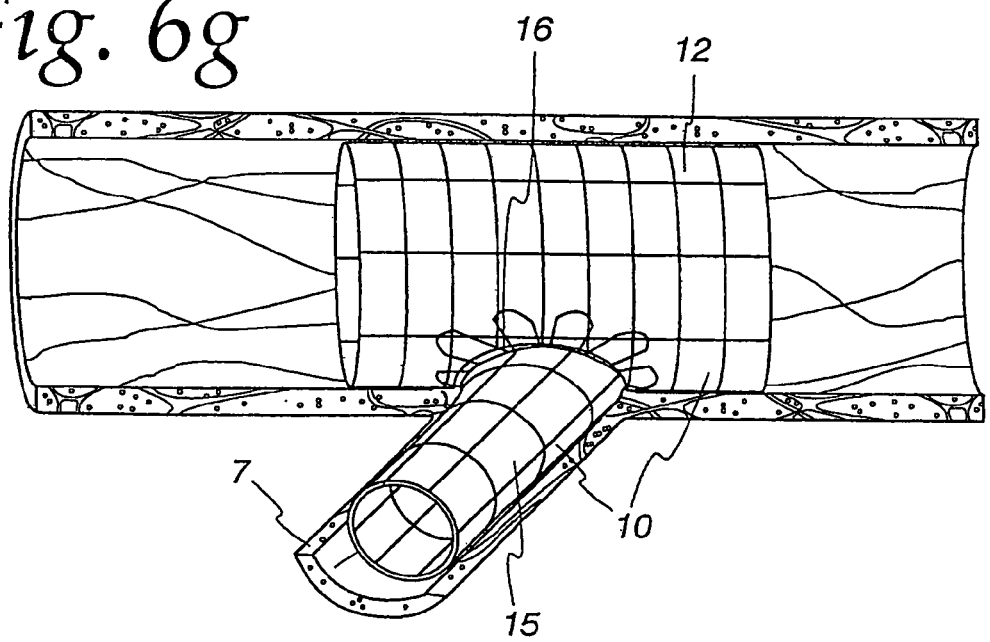
FIG. 6g is a schematic depiction of the fully expanded bifurcating double stent of the invention, positioned into the bifurcation point in a subject vessel.

In the bifurcating double-stent apparatus 10 of the invention, once the main stent 12 is dilated and the stabilizing catheter 44 (as shown in FIG. 6b) is removed, the branch stent 15 is inserted over the branch guidewire 36 and through the opening 16 of the main stent 12 substantially as shown in FIG. 6c, and affixed in place by withdrawal of the protective sheath 34 (FIG. 6d) and insertion of the branch stent 15 until it at least partially contacts the perimeter of the opening 16 of the main stent 12 by the expansion of the contacting portions 18 which are positioned at the proximal end 30 of the expandable stent, as shown in FIG. 6e. The branch stent 15, once positioned in the branch vessel 7, may be then fully expanded by the balloon 25, as shown in FIG. 6f. The angle at which the optionally expandable branch stent 15 is affixed depends upon the vessel structure into which the bifurcating stent apparatus 10 is inserted. All catheters and guidewires are then withdrawn from the subject vessels, leaving the main stent 12 through which the branch stent 15 is inserted into the branch vessel 7, forming a bifurcated stent 10 (FIG. 6g).

Figure 8:
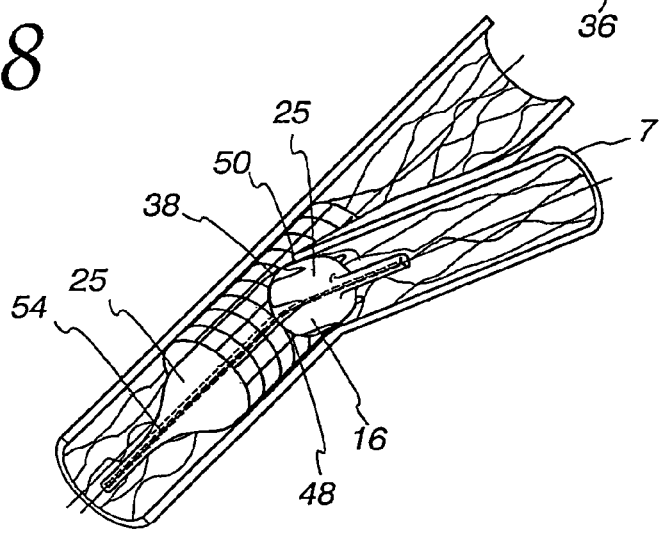
FIG. 8 is a schematic depiction of balloon expansion of the optional expandable portion of the main stent to cover a vessel bifurcation point.
Figure 9:
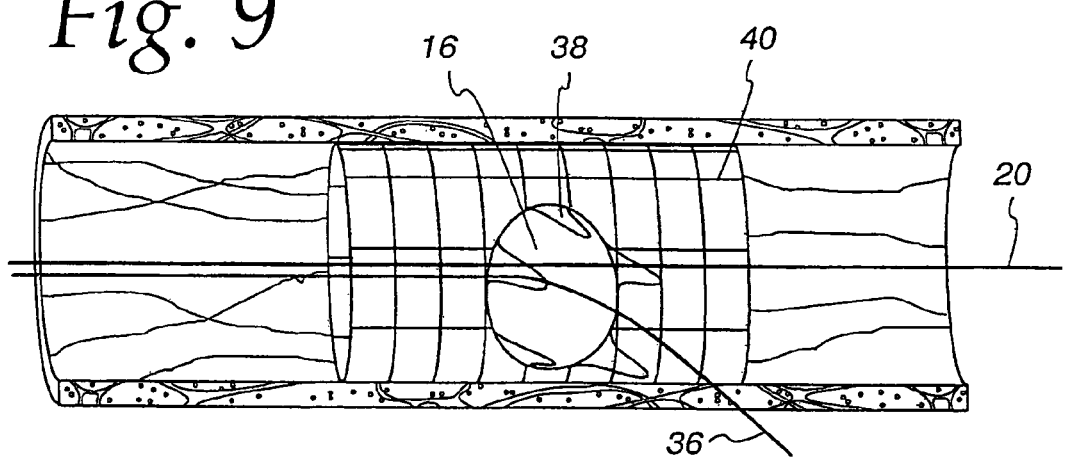
FIG. 9 is a schematic depiction of the main stent with the optional expandable portion fully expanded to extend laterally from the side opening of the main stent.

In the embodiment shown in FIGS. 7-9, the main stent 40 with expandable portion 38 is positioned within the vessel 8 by the guidewires 20 (FIG. 7), and affixed in place by radial expansion of the main stent 40, most particularly by inflation of the balloon 25 (FIG. 8). The main stent is positioned so that the opening 16 is directly over the bifurcation point 50 in the subject vessels 7 and 8 (FIGS. 7 and 8). In order to aid such positioning, a side branch guidewire 36 and a stabilizing catheter 44 (as depicted in FIG. 7) are also inserted through the opening 16 of the main stent 40 and through the expandable portion 38 and into the branch vessel 7 (FIG. 8).

The optional expandable portion 38 of the main stent 40 is then expanded radially and in an at least partially perpendicular manner to the sides of the main stent side opening 16 (FIG. 8). In the embodiment illustrated in FIGS. 7 and 8, a balloon 25 is deployed along the side branch guidewire 36 through the expandable portion 38, and inflated until the expandable portion is fully expanded into the branch vessel 7 to cover the bifurcation point 50 of the branched vessel, as illustrated in FIG. 8. In order to extend the expandable portion 38 into the branch vessel 7, a balloon 25 disposed around a branch catheter 54 which is threaded along the side branch guidewire 36, through the main stent 40, through the opening 16 and expandable portion 38, and into the subject branch vessel 7 as shown in FIG. 8. The expandable portion 38 is then extended into the branch vessel 7 by inflation of the balloon 25, which pushes the expandable portion 38 outward radially and lateral to the side opening, into the branch vessel 7 (FIG. 8). Once all catheters and balloons are withdrawn, the expandable portion 38 is arrayed in lateral orientation to the sides of the opening 16 in the main stent 40, and surrounding the opening 16 into the vessel branch (FIG. 9). The guidewires 20 and 36 are then withdrawn from the main and branch vessels.

In the double stent apparatus of FIG. 5 and in the main stent with expandable portion illustrated in FIGS. 7 and 9, the main stent as well as the expandable portions may be constructed at least partially of imageable material or marked with imageable markers 56 at suitable locations, including around the perimeter of the side openings of the main stent and at the ends of the expandable portions.

When reinforcing a bifurcated vessel where both branches of the vessel require reinforcing, either 1) the single main stent with the expandable portion is used whereby the expandable portion extends into the vessel branch at least partly covering the origin of the bifurcation, which may be used alone or in combination with any conventional stent; or 2) the main stent without the expandable portion and at least one branch stent with contacting portion are used, the branch stent placed to extend through at least one side opening of the main stent into at least one branch vessel, wherein the branch stent is at least partially in registry and contacting the edge of the side opening through which it extends. The branch stent extends laterally at varying angles to the side opening of the main stent. When treating a bifurcated vessel where the area to be treated spans the bifurcation and unobstructed access to the unstented vessel is required, the main stent may be used either with or without the expandable portion, wherein at least one side opening is placed over the bifurcation point.

The stent apparatus of the invention may be constructed from any non-immunoreactive material, including but not limited to any of the materials disclosed in the prior art stents which are incorporated herein by reference. It is intended that the stent apparatuses of the invention may further be at least partially constructed of, or marked at certain points with, a material which may be imaged, most particularly but not limited to by x-ray and ultrasound.

The stents of the invention may be deployed according to known methods utilizing guidewires and catheters, which are then withdrawn from the subject following deployment of the stents. The subject stents may be self-expanding to conform to the shape of the vessel in which they are deployed, or they may be expanded utilizing balloon catheters, or by any other method currently known or developed in the future which is effective for expanding the stents of the invention. It is contemplated that prior to deployment the stents will be in a collapsed state, and will require either mechanical expansion (such as, for example, by balloon expansion) upon deployment or, for self-expanding stents, will require that the stent be confined to the catheter until deployment by, for instance, a retractable sheath, in which the sheath is removed during deployment and the stent self-dilated. The stents of the invention and the optional expandable portion of the main stent of the invention expand radially from their longitudinal axis, lateral to the side opening of the main stent. Other methods of dilation of the stents of the invention may exist, or may become available in the future, and such methods are contemplated as being within the scope of this invention.

It is intended that the invention include all modifications and alterations from the disclosed embodiments that fall within the scope of the claims of the invention.

We claim:

1. A stent for placement in a bifurcated body lumen having a main branch and a side branch, the stent comprising:
   a radially expandable stent body having proximal and distal opposing ends with a body wall having a surface extending therebetween, said body wall defining a plurality of cells and a side opening therethrough, said side opening being larger than each of the cells and configured to allow access to a side branch upon expansion of the stent body, a perimeter of the side opening being continuously concave with respect to a centerpoint of the side opening; and
   an expandable portion extending into said side opening, said expandable portion comprising: a first element, a second element and a third element, each of said elements having two ends, a length as measured between the ends and a width, the length being greater than the width, wherein one of said two ends is integrally formed with the stent body and wherein another of said two ends is unattached to the stent body, and wherein upon expansion the elements extend outwardly relative to the surface of the stent body so as to extend into the side branch while the stent body is within the main branch.

2. The stent of claim 1, wherein the side opening is surrounded by radiopaque markers.

3. The stent of claim 1, wherein the side opening is symmetrical.

4. The stent of claim 1, wherein the side opening is positioned closer to the proximal end than the distal end.

5. The stent of claim 1, wherein the side opening is generally circular in shape.

6. The stent of claim 1, wherein the side opening is generally oval in shape.

7. The stent of claim 1 wherein said stent body is balloon expandable.

8. The stent of claim 1 wherein said stent body is self-expandable.

9. The stent of claim 1 wherein said plurality of elements are balloon expandable.

10. The stent of claim 1 wherein said plurality of elements are self-expandable.

11. The stent of claim 1 wherein the expandable portion further comprises a fourth element.

12. A stent for placement in a bifurcated body lumen having a main branch and a side branch, the stent comprising:
    a radially expandable stent body having proximal and distal opposing ends with a body wall having a surface extending therebetween, said body wall defining a plurality of cells and a side opening therethrough, said side opening being larger than each of the cells and configured to allow access to a side branch upon expansion of the stent body, a perimeter of the side opening being continuously concave with respect to a centerpoint of the side opening; and
    a plurality of expandable elements extending into the side opening in an unexpanded state, each expandable element having a first end attached to the perimeter of the side opening and a second end unattached to the stent body;
    wherein upon expansion, the expandable elements extend outwardly relative to the surface of the stent body so as to extend into the side branch while the stent body is within the main branch.

13. The stent of claim 12 comprising a first expandable element, a second expandable element and a third expandable element.

14. The stent of claim 12, wherein each expandable element has a length that is greater than its width.

15. The stent of claim 12, wherein a length of each expandable element is oriented in a radial direction of the side opening.

16. The stent of claim 1, wherein the length of each of said elements is oriented in a radial direction of the side opening.

* * * * *